United States Patent
Ludescher et al.

(10) Patent No.: US 6,235,897 B1
(45) Date of Patent: May 22, 2001

(54) SEPARATION OF CEPHALOSPORIN ISOMERS

(75) Inventors: Johannes Ludescher, Breitenbach; Harald Summer, Wörgl; Siegfried Wolf, Brixlegg, all of (AT)

(73) Assignee: Biochemie Gesellschaft m.b.H., Kundl (AT)

( * ) Notice: Subject to any disclaimer, the term of this patent is extended or adjusted under 35 U.S.C. 154(b) by 0 days.

(21) Appl. No.: 08/824,100

(22) Filed: Mar. 25, 1997

Related U.S. Application Data

(62) Division of application No. 08/340,580, filed on Nov. 16, 1994, now Pat. No. 5,616,703.

(30) Foreign Application Priority Data

Nov. 17, 1993 (AT) ........................................ 2329/93
Nov. 17, 1993 (AT) ........................................ 2330/93

(51) Int. Cl.$^7$ ................................................. E07D 501/18
(52) U.S. Cl. ............................................................ 540/226
(58) Field of Search ................................................ 540/226

(56) References Cited

U.S. PATENT DOCUMENTS 5,073,551  12/1991  Kabori et al. ........................ 514/206

FOREIGN PATENT DOCUMENTS

| | | |
|---|---|---|
| 900544A | 3/1985 | (BE) . |
| 614447 | 11/1979 | (CH) . |
| 26044 | 4/1981 | (EP) . |
| 0175610 | 3/1986 | (EP) . |
| 0236231 | 9/1987 | (EP) . |
| 0420608 | 4/1991 | (EP) . |
| 0503453 | 9/1992 | (EP) . |
| 594099A1 | 4/1994 | (EP) . |
| 0597429 | 5/1994 | (EP) . |
| 2264944 | 9/1993 | (GB) . |
| 6041145 | 2/1994 | (JP) . |
| 7311575 | 2/1974 | (NL) . |
| 9316084 | 8/1993 | (WO) . |
| 9325557 | 12/1993 | (WO) . |

OTHER PUBLICATIONS

The Journal of Antibiotics vol. XLIII No. 8 (Aug. 1990) p. 1047–1050.
Chem. Pharm. Bulletin—39 (9) 2433–2436 (1991).
Drugs of the Future (1992) 17 (8); 665–671.
Communication—EP 94 11 8048 (4 pages) Search Report (Apr. 11, 1995).

*Primary Examiner*—John M. Ford
(74) *Attorney, Agent, or Firm*—Susan Hess

(57) ABSTRACT

Process of depleting 7-amino-3-[(E)-2-(4-methyl-5-thiazolyl)vinyl]-3-cephem-4-carboxylic acid in Z/E mixtures of 7-amino-3-[2-(4-methyl-5-thiazolyl)vinyl]-3-cephem-4-carboxylic acid a) by subjecting an amine salt of a Z/E mixture of 7-amino-3-[2-(4-methyl-5-thiazolyl)vinyl]-3-cephem-4-carboxylic acid to crystallization and converting this amine salt into 7-amino-3-[2-(4-methyl-5-thiazolyl)vinyl]-3-cephem-4-carboxylic acid, or b) by subjecting the Z/E mixture to chromatography.

3 Claims, No Drawings

SEPARATION OF CEPHALOSPORIN ISOMERS

This is a division of application Ser. No. 08/340,580, filed Nov. 16, 1994, now U.S. Pat. No. 5,616,703.

The invention relates to a process of depleting the E-(trans) isomer amount in Z/E (cis/trans) 7-amino-3-[2-(4-methyl-5-thiazolyl)vinyl]-3-cephem-4-carboxylic acid of formula

I

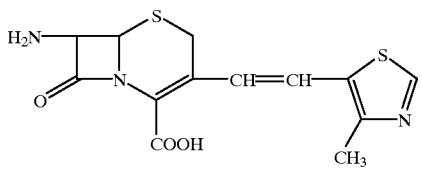

It is known that the Z-configuration represents the characteristic which determines the advantageous properties of cephalosporin end products in the Gram negative range. Consequently, an active compound with the smallest possible content of E-isomer is desired for optimum efficiency.

Synthetic processes for the production of these antibiotics or intermediates thereof yield Z-isomers in admixture with E-isomers.

In example 37 of EP 0 420 608 the production of 7-β-phenylacetamido-3-[2-(4-methyl-5-thiazolyl)vinyl]-3-cephem-4-carboxylic acid-4-methoxybenzylester is described. According to the $^1$H-NMR data given therein, a mixture of the Z/E-isomers is obtained. During production of the desired active compound the isomeric mixture is retained. According to Journal of Antibiotics Vol. XLIII, No. 8, pages 1047–1050, (1990), 7-β-phenylacetamido-3-[2-(4methyl-5-thiazolyl)vinyl]-3-cephem-4-carboxylic acid-4-methoxybenzylester is obtained with a Z/E ratio of 4.7/1. It is pointed out that the isomers at this stage are difficult to separate. Separation is therefore carried out at a later stage, after removing the phenylacetyl group, reacylating with the protected side chain of the active substance, and removing the protecting groups.

In Chem. Pharm. Bull. 39(9), 2433–2436, (1991) the production of the pure Z-isomer of 7-β-phenylacetyl-3-[2-(4-methyl-5-thiazol)vinyl]-3-cephem-4-carboxylic acid-4-methoxybenzylester from the resultant Z/E-isomeric mixture by partially separating the E-isomer by crystallization and subsequently effecting chromatography on silica gel with benzene and ethyl acetate is described. The solvent mixture used for chromatography and the chromatography material may only be regenerated with difficulty and benzene is a solvent, which should no longer be used due to its carcinogenity.

According to reference example 1 of EP 0 236 231 the analogous benzhydrylester is obtained in pure Z-form, but also only by use of benzene/ethyl acetate as the eluant in the chromatography step. In reference example I of EP 0 175 610, the separation of the pure Z-isomer of 7-phenoxyacetamido-3-[2-(4methyl-5-thiazolyl)vinyl]-3-cephem-4-carboxylic acid benzhydrylester is described in the same manner.

A further process for the production of the compounds of formula I, described in EP 597 429, takes place in accordance with the following reaction scheme:

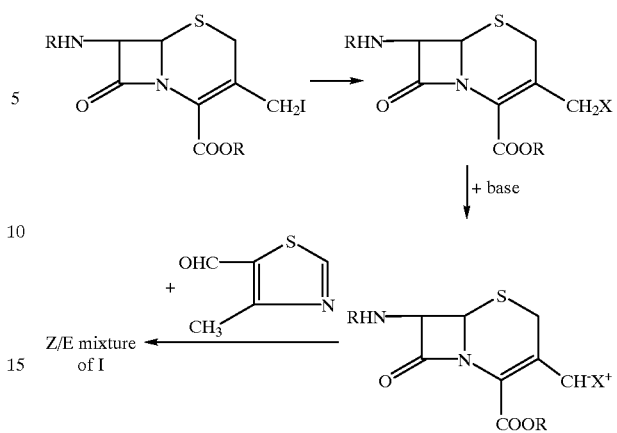

In this formula scheme, R is a silyl protecting group, X is $-P^+(R_4)_3I^-$ or $-P(O)(OR_4)_2$ and $X^+$ is $-P^+(R_4)_3$ or $-P(O)(OR_4)_2Y$. $R_4$ denotes a lower alkyl group or an aryl group and Y denotes a cation from the alkali series or the protonated form of an organic base. Z/E mixtures of compounds of formula I with an E content of about 20% and more and their preparation are described.

According to the invention in one aspect we have surprisingly found that the Z- (cis) isomer of 7-amino-3-[2-(4methyl-5-thiazolyl)vinyl]-3-cephem-4-carboxylic acid of formula Ia

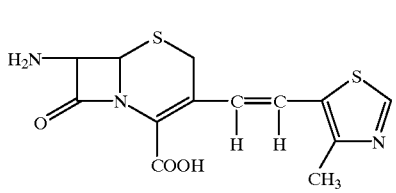

in which the hydrogen atoms at the C=C bond have cis configuration or a Z/E mixture e.g. with a high content of Z isomer may be used as a central intermediate compound in the production of highly effective broad-spectrum antibiotics, for example cefditoren pivoxil of formula

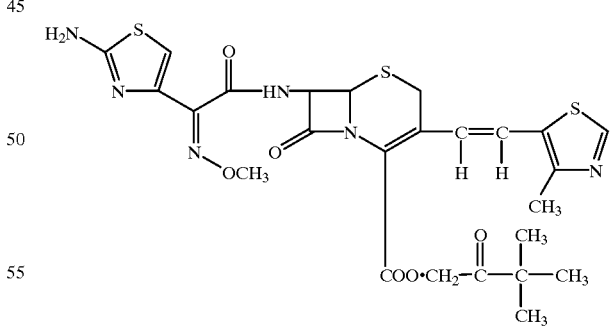

In another aspect we have surprisingly found that Z/E mixtures of, in position 4 and 7 unprotected, 7-amino-3-[2-(4-methyl-5-thiazolyl)vinyl]-3-cephem-4-carboxylic acid having a certain E content may be converted into 7-amino-3-[2-(4-methyl-5-thiazolyl)vinyl]-3-cephem-4-carboxylic acid having a lower E content via an amine salt or via chromatography.

In one aspect the invention provides therefore simple and efficient methods of depleting 7-amino-3-[(E)2-(4-methyl- 5-thiazolyl)vinyl]-3-cephem-4-carboxylic acid in Z/E mixtures of 7-amino-3-[2-4-methyl-5-thiazolyl)vinyl]-3-cephem-4carboxylic acid a) by subjecting an amine salt of a Z/E mixture of 7-amino-3-[2-(4-methyl-5-thiazolyl)vinyl]-3-cephem-4-carboxylic acid to crystallization and converting this amine salt into 7-amino-3-[2-(4-methyl-5-thiazolyl)vinyl]-3-cephem-4-carboxylic acid, or b) by subjecting the Z/E mixture to chromatography.

The process may be a separation process, e.g. for at least partial separation of the E- and Z-isomer and/or to lower, i.e. to deplete the content of the E-isomer in Z/E mixtures, e.g. to enhance the Z content or to provide the pure Z-isomer.

Process a) may be effected as follows:

The amine salt may be formed in a protic or in an aprotic solvent. A compound of formula I may be admixed with an amine, an organic solvent or solvent mixture and optionally water, resulting in a solution or a suspension. Suitable organic solvents are for example alcohols, e.g. methanol, ethanol, one of the isomeric propanols or butanols; ketones, e.g. acetone or methyl ethyl ketone; amides, e.g. dimethylformamide; esters, e.g. ethyl acetate, isopropyl acetate, butyl acetate; nitriles, for example acetonitrile;

optionally in the presence of water; or mixtures of the above solvents; particularly, for example acetone; acetone and water; methanol; methanol and acetone. The mixture may optionally be diluted with a further solvent or solvent mixture, i.e. a solvent or solvent mixture which has poorer solubility for the Z-isomer of the compound of formula II, hereinafter called "counter solvent". Counter solvents are for example the solvents given above with the exception of amides but with the addition of ethers, e.g. tert. butyl methyl ether, diethylether, tetrahydrofuran and mixtures of such solvents. Conveniently a solvent which may also be used as counter solvent may be used.

Alternatively process a) may be effected as follows:

A Z/E mixture of an amine salt of 7-amino-3-[2-(4-methyl-5-thiazolyl)vinyl]-3-cephem-4-carboxylic acid may be dissolved or suspended in a solvent or solvent mixture, and the solubilizing power of the mixture (solubility product) may be optionally readjusted by adding a counter solvent as described above. Solvents and counter solvents which may be used are given above.

Conveniently a solvent which may also be used as counter solvent may be used.

The solvent may be chosen so that the amine salt of 7-amino-3-[2-(4-methyl-5-thiazolyl)vinyl]-3-cephem-4carboxylic acid having a lower content of E-isomer than the Z/E mixtures of 7-amino-3-[2-(4-methyl-5-thiazolyl)vinyl]-3-cephem-4-carboxylic acid used as starting material crystallizes out.

Examples of amines useful in the process of the invention are amines of formula

NR₁R₂R₃ wherein $R_1$, $R_2$ and $R_3$ are the same or different and independently of one another denote hydrogen, $(C_{1-8})$alkyl, unsubstituted or substituted benzyl or $(C_{4-8})$cycloalkyl, or $R_1$ and $R_2$ together with the nitrogen atom signify a 5- or 6-membered heterocycle, which may contain one or two further hetero atoms, and $R_3$ is as defined above, for example tert. butylamine, benzylamine, dibenzylamine, dicyclohexylamine, tert.-octylamine (=2,4,4-trimethylpentyl-2-amine), particularly tert. butylamine, dicyclohexylamine, tert.-octylamine.

If a benzyl or dibenzylamine is used the benzyl group may be unsubstituted or substituted by groups which are inert under the reaction conditions. Such groups are for examples $(C_{1-8})$alkyl, $(C_{1-8})$alkoxy or alkylthio, halogen, nitro, sulfoxy groups.

If $R_1$ together with $R_2$ and the nitrogen atom signify a 5- or 6-membered heterocycle, containing optionally 1 or additional heteroatoms, these are for example nitrogen, oxygen or sulphur atoms. Examples of such heterocycles are morpholine, N-methyl-morpholine, oxazolidine or thiazolidine.

The amine of formula III is for example employed in stoichiometric quantities or in an excess of the compound to be purified.

The amine salt according to the present invention may be easily converted into compounds of formula I with a reduced E content or into the pure Z compound of formula Ia by treatment with an acid. This may be effected by dissolving or suspending the amine salt in water and by acidifying, for example by adding an acid such as hydrochloric acid, phosphoric acid or sulphuric acid. The amine which is set free may optionally be removed by extraction in a first alkaline step or kept in solution by addition of an organic solvent such as an alcohol or a ketone. The crystalline compound of formula I or the crystalline compound of formula Ia is subsequently filtered off and dried.

Process a) has several advantages. The amine salts are easily precipitated and crystallized. This process is especially advantageous in the production of cephalosporins when applied to Z/E mixtures of formula I with a high E-content and /or containing by products, e.g. those obtained from early eluting fractions from process b), effording products with a low E-content and high purity. This has also the advantage of an improved total yield. Process steps a) may be optionally repeated in order to obtain the desired Z/E ratio.

An amine salt of 7-amino-[3-2-(4-methyl-5-thiazolyl)vinyl]-3-cephem-4-carboxylic acid, in particular compounds of formula

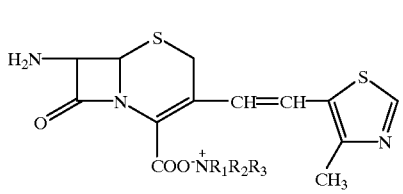

II wherein $R_1$, $R_2$ and $R_3$ have the meaning given above are new and also form part of the invention; especially compounds of formula II wherein the hydrogen atoms at the C=C bond have the cis configuration. These amine salts surprisingly facilitate the separation of Z/E mixtures of 7-amino-[3-2-(4-methyl-5-thiazolyl)vinyl]-3-cephem-4-carboxylic acid.

Process step b) may be carried out as follows:

The compound of formula I may be dissolved, for example in water and for example by adding a base, e.g. ammonia, or an inorganic acid, e.g. hydrochloric acid and is subjected to chromatography, for example to adsorption chromatography. Adsorbents include adsorber resins, for example ionic exchange resins, for example such as sold as HP-20, HP-21 or SP 207 (from Mitsubishi), XAD-1180, XAD-1600 or XAD-16 (e.g. Rohm-Haas) or Amberchrom CG-161 (Toso-Haas), especially XAD-1600 and Amberchrom CG-161 or activated carbon, e.g. sold as Norit CG-1, SX-plus, C-granular or Cecarbon GAC 40. Elution may be effected with water or a solvent/water mixture. Solvents may be for example alcohols, such as methanol, ethanol and isopropanol, or ketones, for example acetone, particularly alcohol. In this process the E-isomer has a better adsorption than the Z-isomer and thus is more slowly eluted than the Z-isomer. The first eluted fractions contain therefore mainly the Z-isomer, whereas the latest fractions contain mainly the E-isomer. The desired product may be obtained by adjusting the pH value close to the isoelectric point of the compound of formula I, i.e. 2.5 to 4.5, particularly to 3.0 to 3.7. Crystallization may occur. Depending i.a. on which fractions are combined, products with a very low amount of E-isomer or products with a higher content of E-isomer are obtained. In any case the content of the E-isomer in the product of the process of the invention is lower than the content in the starting Z/E mixture.

The amount of the adsorbent depends i.a. on the desired dissolution rate and the Z/E ratio of the starting compound of formula I.

Process b) represents a very simple, economical and ecologically acceptable method. The elution may be effected with water and optionally alcohol, which are ecologically acceptable solvents. The adsorbents may be regenerated for example by washing with water or alcohol. Alcohol/water mixtures may be readily regenerated. The equipment is simple. No gradient elution or stepwise elution and no changes of the pH are necessary.

Processes a) and b) may conveniently be combined.

The compound of formula I having a low E content or its amine salts may be prepared as described by the processes herein containing various amounts of Z/E isomers, e.g. in a ratio of 86:14 or less, 91:9 or less, 92:8 or less, 96:4 or less, or 98:2 or less; e.g. undetectable by $^1$H-NMR; for example a compound of formula Ia and of formula II having an undetectable E-content may be prepared. Compounds of formula I which are used as starting material in the process according to the present invention may contain any Z/E ratio but at least a detectable amount of Z as well as of E. Processes a) and b) are suitable for industrial scale Z/E mixtures of the compounds of formula I having a high content of the E-isomer may be prepared according to known methods.

The compound of formula Ia and the compounds of formulae I with a content of E-isomer of 15% and less are new and form also part of the invention.

The compounds of formula I with a low E content and the compound of formula Ia are ideal starting materials for the production of cefditoren pivoxil and similar active compounds having the same substitution pattern in position 3. A wide variety of derivatives in position 7 and position 4 (carboxylic acid) may be produced, and their production in pure form according to the invention takes place very simply and economically.

Details of resins are known, e.g. from manufacture's brochures.

In the following examples, which illustrate the invention in detail, all temperatures are given in degrees Celsius. Trimethylsilylpropionic acid-$d_4$ is used as standard ($^1$H-NMR).

EXAMPLE 1

Depletion of 7-amino-3-[(E)-2-(4-methyl-5-thiazolyl) vinyl]-3-cephem-4-carboxylic acid in (Z/E) 7-amino-3-[2-(4-methyl-5-thiazolyl)vinyl]-3-cephem-4-carboxylic acid by use of the dicyclohexylammonium salt a) 3 g of (Z/E) 7-amino-3-[2-(4-methyl-5-thiazolyl) vinyl]-3-cephem-4-carboxylic acid with an E content of ca. 14% ($^1$H-NMR) are introduced into a mixture of 6 ml of water and 15 ml of acetone. The suspension is heated to 30°. 2.04 ml of dicyclohexylamine are added, and the mixture is stirred until a practically clear solution is obtained. The heating is removed, a few seed crystals are added, and the resultant suspension is stirred for 15 minutes at room temperature. 21 ml of acetone are added in drops over the course of 15 minutes, and the reaction mixture is subsequently placed in an ice bath for 2 hours. The dicyclohexylammonium salt is isolated through a suction filter, washed with a total of 20 ml of acetone, and dried in a vacuum over night.

E content ($^1$H-NMR): ca. 9%

$^1$H-NMR (D$_2$O): 1.13–1.34 (m, 10H, cyclohexyl); 1.65–1.69 (m, 2H, cyclohexyl); 1.82 (s, broad, 4H, cyclohexyl); 2.04 (m, broad, 4H, cyclohexyl); 2.39 (s, 3H, CH$_3$, Z); 2.43 (s, 3H, CH$_3$, E); 3.2–3.3 (m, 2H, cyclohexyl); 3.32, 3.57 (ABq, J=18.3 Hz, 2H, SCH$_2$, Z); 3.68, 3.84 (ABq, J=17.3 Hz, 2H, SCH$_2$, E); 4.80–5.22 (m, 2H, H-6, H-7, Z and E); 4.81 (s, broad, HOD); 6.32, 6.64 (ABq, J=11.7 Hz, 2H, CH=CH, Z); 6.86, 7.05 (ABq, J=16.1 Hz, 2H, CH=CH, E); 8.74 (s, 1H, CH=N, E); 8.78 (s, 1H, CH=N, Z).

2 g of the dicyclohexylammonium salt obtained under a) are dissolved in 60 ml of water at ca. 30°, and the pH value is slowly adjusted to 3.5 by use of diluted sulphuric acid. The suspension is stirred for a further 30 minutes whilst cooling with ice. The crystalline free acid is subsequently suctioned off through a filter, washed with water and acetone, and dried.

E content ($^1$H-NMR): ca. 9%

$^1$H-NMR (D$_2$O/K$_2$CO$_3$): 2.38 (s, 3H, CH$_3$, Z); 2.42 (s, 3H, CH$_3$, E); 3.32, 3.57 (ABq, J=18 Hz, 3H, SCH$_2$, Z); 3.67, 3.82 (ABq, J=17 Hz, 3H, SCH$_2$, E); 4.81 (s, broad, HOD); 5.1–5.5 (m, 2H, H-6, H-7, Z+E); 6.31, 6.64 (ABq, J=12 Hz, 2H, CH=CH, Z); 6.83, 7.02 (ABq, J=16 Hz, 2H, CH=CH, E); 8.72 (s, 1H, S—CH=N, E); 8.77 (s, 1H, S—CH=N, Z).

b) 1 g of (Z/E) 7-amino-3-[2-(4-methyl-5-thiazolyl) vinyl]-3-cephem-4-carboxylic acid with an E content of ca. 9% is introduced into a mixture of 2 ml of water and 5 ml of acetone. 0.68 ml of dicyclohexylamine are added. A practically clear solution results from which crystallization starts. The suspension is left to stand at room temperature for 15 minutes, then stirred for a further 15 minutes, and then 7 ml of acetone are slowly added. After cooling for a further 2 hours in an ice bath, the dicyclohexylammonium salt is isolated, washed with 5 ml of acetone and dried.

$^1$H-NMR (D$_2$O): 1.13–1.34 (10H, cyclohexyl); 1.65–1.69 (2H, cyclohexyl); 1.82 (s, broad, 4H, cyclohexyl); 2.04 (s, broad, 4H, cyclohexyl); 2.39 (s, 3H, CH$_3$); 3.2–3.3 (m, 2H, cyclohexyl); 3.32, 3.57 (ABq, J=18.3 Hz, 2H, SCH$_2$); 4.80, (d, J=4.9 Hz, 1H, β-lactam); 4.81 (s, broad, HOD); 5.21 (d, J=4.9 Hz, 1H, β-lactam); 6.32, 6.64 (ABq, J=11.7 Hz, 2H, CH=CH); 8.78 (s, 1H, CH=N).

E content ($^1$H-NMR): undetectable 0.8 g of the dicyclohexylammonium salt obtained according to b) are dissolved in 30 ml of water at 30°. The mixture is acidified to pH 3.5 whilst stirring with diluted sulphuric acid, and the crystalline deposit is isolated after standing for 30 minutes in an ice bath. The product (free acid) is washed with water and acetone, and dried. Melting point: >200° (decomposition).

$^1$H-NMR (D$_2$O/K$_2$CO$_3$): 2.38 (s, 3H, CH$_3$); 3.32, 3.57 (ABq, J=18.3 Hz, 2H, SCH$_2$); 4.80 (d, J=4.9 Hz, 1H, β-lactam); 4.81 (s, broad, HOD); 5.21 (d, J=4.9 Hz, 1H, P-lactam); 6.31, 6.64 (ABq, J=11.7 Hz, 2H, CH=CH); 8.77 (s, 1H, SCH=N).

E content ($^1$H-NMR): undetectable.

EXAMPLE 2

Depletion of 7-amino-3-[(E)-2-(4methyl-5-thiazolyl)vinyl]-3-cephem-4-carboxylic acid in (Z/E) 7-amino-3-[2-(4-methyl-5-thiazolyl)vinyl]-3-cephem-4carboxylic acid by use of the tert.-octylammonium salt 6 g of (Z/E) 7-amino-3-[2-(4-methyl-5-thiazolyl)vinyl]-3-cephem-4-carboxylic acid with an E content of ca. 13% ($^1$H-NMR) are introduced into a mixture of 12 ml of water and 30 ml of acetone. The suspension is heated to 30°. 3.4 ml of tert.-octylamine are added, and the mixture is stirred for 30 minutes at room temperature. 42 ml of acetone are added in drops over the course of 15 minutes and the reaction mixture is subsequently placed in an ice bath for 2 hours. The tert.-octylammonium salt is isolated through a suction filter, washed with a total of 20 ml of acetone, and dried in a vacuum overnight. Melting point: 195–199° (decomposition)

$^1$H-NMR D$_2$O ): 1.05 (s, 9H, C(CH$_3$)$_3$, tert.-octyl); 1.45 (s, 6H, C(CH$_3$)$_2$, tert.-octyl); 1.68 (s, 2H, CH$_2$, tert.-octyl); 2.24 (s, CH$_3$, acetone); 2.40 (s, 3H, CH$_3$); 3.34, 3.60 (ABq, J=18.1 Hz, 2H, SCH$_2$); 4.80 (under HOD, 1H, P-lactam); 4.81 (s, broad, HOD); 5.22 (d, J=5.0 Hz, 1H, β-lactam); 6.33, 6.67 (ABq, J=11.6 Hz, 2H, CH=CH); 8.79 (s, 1H, CH=N).

E content ($^1$H-NMR): undetectable 6 g of the tert.-octylammonium salt thus obtained are mixed with 180 ml of water and with about 100 ml of methanol at room temperature whilst stirring, until a solution is obtained. The pH value is slowly adjusted to 3.5 with diluted sulphuric acid. The suspension is stirred for a further 30 minutes whilst cooling with ice. The crystalline free acid is suctioned off through a filter, washed with water and acetone and dried.

$^1$H-NMR as example 1a)

E content ($^1$H-NMR): undetectable

EXAMPLE 3

Depletion of 7-amino-3-[(E)-2-(4-methyl-5-thiazolyl)vinyl)-3-cephem-4-carboxylic acid in (Z/E) 7-amino-3-[2-(4methyl-5-thiazolyl)vinyl]-3-cephem-4-carboxylic acid by use of the tert.-butylammonium salt 0.5 g of (Z/E) 7-amino-3-[2-(4-methyl-5-thiazolyl)vinyl]-3-cephem-4-carboxylic acid with an E content of ca. 25% ($^1$H-NMR) are added to a mixture of I ml of water and 5 ml of acetone. 0.2 g of tert.-butylamine are added and a clear solution is formed which is stirred for 30 minutes at room temperature. 10 ml of acetone are added and the reaction mixture is subsequently placed in an ice bath for 2 hours. The tert.-butylammonium salt is isolated through a suction filter, washed with a total of 5 ml of acetone and dried in a vacuum overnight.

$^1$H-NMR (D$_2$O ): 1.34 (s, 9H, C(CH$_3$)$_3$, tert.-butyl); 2.35 (s, 3H, CH$_3$, Z and E); 3.30, 3.54 (ABq, J=18.1 Hz, 2H, SCH$_2$, Z); 3.6, 3.8 (ABq, 2H, SCH$_2$, E); 4.78 (d, J=5.0 Hz, 1H, β-lactam, Z); 4.81 (s, broad, HOD); 5.1 (d, 1H, β-lactam, E); 5.18 (d, J=5.0 Hz, 1H, β-lactam, Z); 6.28, 6.61 (ABq, J=11.6 Hz, 2H, CH=CH, Z); 6.8, 7.0 (ABq, 2H, CH=CH, E); 8.7 (s, 1H, CH=N, E); 8.74 (s, 1H, CH=N, Z).

E content ($^1$H-NMR): ca. 4%

EXAMPLE 4

Depletion of 7-amino-3-[(E-2-(4methyl-5-thiazolyl)vinyl]-3-cephem-4-carboxylic acid in (Z/E) 7-amino-3-[2-(4-methyl-5-thiazolyl)vinyl]-3-cephem-4-carboxylic acid by chromatography 10 g of (Z/E) 7-amino-3-[2-(4methyl-5-thiazolyl)vinyl]-3-cephem-4-carboxylic acid with an E content of ca. 23% ($^1$H-NMR) are suspended in 100 ml of water and 25 ml of acetone and acidified with aqueous hydrochloric acid to a pH value of 0.8 whilst cooling with ice. The cloudy solution is filtered over 3 g of activated carbon and the carbon is washed with 10 ml of water, containing a few drops of hydrochloric acid. The eluate is slowly adjusted to a pH value of 3.5 with 2 N NaOH and the product precipitates. The mixture is stirred for another one hour whilst cooling with ice. The precipitated free acid is filtered, washed with water and acetone and dried.

E content ($^1$H-NMR):ca. 14%

EXAMPLE 5

Depletion of 7-amino-3-[(E)-2-(4-methyl-5-thiazolyl)vinyl]-3-cephem-4-carboxylic acid in (Z/E) 7-amino-3-[2-(4-methyl-5thiazolyl)vinyl]-3-cephem-4-carboxylic acid by chromatography 1 g of (Z/E) 7-amino-3-[2-(4-methyl-5-thiazolyl)vinyl]-3-cephem-4-carboxylic acid with an E-content of ca. 24% ($^1$H-NMR) is mixed with 10 ml of water and with a little ammonia (pH 8). The solution is then transferred onto a column which is filled with 100 ml of Amberchrom® CG-161 and is eluted with 2% by volume of isopropanol in water. Fractions containing less than 4% E-isomer are collected, concentrated to a volume of about 30 ml by evaporation, and adjusted to pH 3 with hydrochloric acid. The mixture is stirred for 1 hour in an ice bath, the deposit (free acid) is filtered off, washed with water and dried.

E content ($^1$H-NMR): ca. 2%

What is claimed is:

1. 7-amino-3-{(Z)2-(4-methyl-5-thiazolyl)vinyl}3-cephem-4-carboxylic acid dicyclohexylammonium salt.

2. 7-amino-3A(Z)-2-(4-methyl-5-thiazolyl)vinyl}-3-cephem-4-carboxylic acid (2,4,4,-trimethylpentyl-2) ammonium salt.

3. 7-amino-3-{((Z)-2-(4-methyl-5-thiazolyl)vinyl}-3-cephem-4-carboxylic acid tert.-butylammonium salt.

* * * * *

UNITED STATES PATENT AND TRADEMARK OFFICE
CERTIFICATE OF CORRECTION

PATENT NO. : 6,235,897 B1
DATED : May 22, 2001
INVENTOR(S) : Johannes Ludescher et al.

It is certified that error appears in the above-identified patent and that said Letters Patent is hereby corrected as shown below:

Column 8, claim 1,
Line 50, "7-amino-3-{(Z)2-(4-methyl-5-thiazolyl)vinyl)3-" should read -- 7-amino-3-{(Z)-2-(4-methyl-5-thiazolyl)vinyl}-3- --

Column 8, claim 2,
Line 52, "7-amino-3A(Z)-2-(4-methyl-5-thiazolyl)vinyl}-3-" should read -- 7-amino-3-{(Z)-2-(4-methyl-5-thiazolyl)vinyl}-3- --

Column 8, claim 3,
Line 55, "7-amino-3-{((Z)-2-(4-methyl-5-thiazolyl)vinyl}-3-" should read -- 7-amino-3-{(Z)-2-(4-methyl-5-thiazolyl)vinyl}-3- --

Signed and Sealed this

Fifth Day of March, 2002

Attest:

*Attesting Officer*

JAMES E. ROGAN
*Director of the United States Patent and Trademark Office*